United States Patent

Saadat

[11] Patent Number: 5,827,269
[45] Date of Patent: Oct. 27, 1998

[54] HEATED BALLOON HAVING A RECIPROCATING FLUID AGITATOR

[75] Inventor: Vahid Saadat, Redwood Shores, Calif.

[73] Assignee: Gynecare, Inc., Menlo Park, Calif.

[21] Appl. No.: 775,491

[22] Filed: Dec. 31, 1996

[51] Int. Cl.⁶ .................................................. A61F 7/12
[52] U.S. Cl. .............................................. 606/28; 607/105
[58] Field of Search .................................... 607/105, 113; 606/27–32, 192, 193; 604/96–100

[56] References Cited

U.S. PATENT DOCUMENTS

| | | | |
|---|---|---|---|
| 1,690,926 | 11/1928 | Dequer | 607/113 |
| 3,174,481 | 3/1965 | Seaman | 607/105 |
| 4,949,718 | 8/1990 | Neuwirth et al. | 607/105 |
| 5,084,044 | 1/1992 | Quint | 607/105 |
| 5,460,628 | 10/1995 | Neuwirth et al. | 607/105 |
| 5,571,153 | 11/1996 | Wallsten | 606/28 |
| 5,653,692 | 8/1997 | Masterson et al. | 607/113 |
| 5,704,934 | 1/1998 | Neuwirth et al. | 607/105 |
| 5,713,942 | 2/1998 | Stern et al. | 607/113 |

*Primary Examiner*—Mark S. Graham

[57] ABSTRACT

An apparatus for thermal coagulation and more particularly to a system for applying heat to the endometrium of a human uterus of the type comprising a heated balloon catheter having a reciprocating piston for improved circulation of fluid within a distensible bladder. The present invention includes a heated balloon catheter having a fluid delivery tube connected to a distensible bladder. The catheter further includes a reciprocating piston which moves along a linear path within the distensible bladder to cause vigorous fluid agitation therein. The agitation caused by the piston efficiently mixes the fluid within the balloon without requiring hot fluid to circulate through the fluid delivery tube.

22 Claims, 7 Drawing Sheets

HEATED BALLOON HAVING A RECIPROCATING FLUID AGITATOR

BACKGROUND OF THE INVENTION

The present invention relates generally to an apparatus for thermal coagulation and more particularly to a system for applying heat to the endometrium of a human uterus of the type comprising a heated balloon catheter having a rotary impeller for improved circulation of fluid within a distensible bladder.

The following terms as used herein have the meaning given below:

"Menorrhagia" means a condition of excessive menstrual bleeding in women.

"Thermal coagulation" means the application of heat to tissue in an amount sufficient to destroy the tissue.

"Necrosis" means the death of cells in tissue.

"Endometrium" is that portion of the inner lining of the uterus to which an embryo normally attaches and is responsible for the menstrual cycles.

Apparatus and methods utilizing heated balloons or similar distensible bladders have been used to treat menorrhagia in women. Patients and physicians may prefer treatment of menorrhagia with a heated balloon, because such a minimally invasive procedure effectively curtails the excessive uterine bleeding associated with menorrhagia without requiring surgical removal of the uterus. Such balloon therapy involves inserting and inflating a balloon with a fluid into the uterus. After balloon inflation, the fluid is heated to a temperature for a period of time that coagulates, ablates, necroses, or destroys the endometrium (mucous membrane) and perhaps a portion of the myometrium (muscular layer). A successful endometrial ablation procedure requires controlling the temperature of the balloon. If the heating of the endometrial lining continues longer than necessary for thermal coagulation of the endometrium, then the myometrium could be irreparably damaged.

Temperature fluctuations and gradients along the surface of the balloon adversely affects an operator's control over endometrial thermal coagulation. Temperature fluctuations and gradients are, in part, caused by convection currents of the fluid within the balloon and the presence of an insulating, static boundary layer of fluid along the inner wall of the balloon. While cooler fluid moves toward the bottom of the balloon, the warmer, less dense fluid rises. When the fluid within the balloon is subject to such convection during heating, considerable temperature fluctuations along the surface of the balloon may result, causing less than optimal results. Mechanical circulation or agitation of fluid within the balloon has been known to improve the temperature consistency over the surface of the balloon.

Some balloon catheters circulate fluid by means of separate inlet and outlet passages that connect the balloon with an external heating element. Heat is circulated from the external heating element through the inlet passage into the balloon. Then, the fluid from the balloon is returned to the external heating element through the outlet passage. Such a catheter design requires the hot fluid to pass through the vagina and the opening of the cervix, which may cause physical discomfort or possible tissue damage as heat is conducted through the catheter walls. Since the hot fluid must travel a significant distance between the external heating element and the balloon surface being heated, control over temperature of the balloon surface is difficult.

Other known heated balloon catheters circulate fluid via a pair of one way valves mounted within a housing located at the end of a fluid delivery tube. The housing is surrounded by an inflatable member, such as a balloon. The first valve permits fluid flow from the housing into the balloon. The second valve permits flow from the balloon into the housing. The valves respond to alternating pressure differentials between the balloon and the housing created by an external bellows or piston which causes pulses of fluid to move up and down the fluid delivery tube. Such a configuration requires circulating hot fluid from the balloon into the fluid delivery tube, creating a risk of causing discomfort to the patient or vaginal tissue damage.

Another balloon catheter design known in the art places a propeller or pump wheel within a lumen of a tubular housing contained within the balloon. Such a configuration creates axial fluid motion or motion substantially parallel to the axis of rotation. However, because the propeller is contained within the housing, any axial fluid flow results in mostly linear flow through the tubular housing and a generally linear current within the balloon. Thus, the heating of the balloon surface may not be uniform and the fluid may not properly circulate around the cornua of the uterus where the endometrium is usually the thickest. Another problem with this approach is the lack of sufficient cross section of the lumen to prevent a sufficiently low resistance to passing the fluid through the housing and into the balloon. Thus, vigorous circulation may not be possible so as to prevent a boundary layer of fluid from forming along the inner surface of the balloon.

Other balloon catheter configurations which have limited effectiveness or practicality are known. One such design places a longitudinally vibrating member at the end of a heating element within a balloon. Another design places a flat shape memory alloy at the end of the heating element, such that the shape memory alloy responds to electrical impulses to move the alloy in a lateral fanning motion, thereby somewhat circulating the fluid within the balloon. Each of these designs may work with varying degrees of effectiveness, but have yet to provide a practical configuration and cost effective solution for providing uniform heating of the balloon surface. Thus, heretofore, there was a need for a circulation system that causes vigorous agitation of fluid within the distensible bladders of a balloon catheter in a safe and effective manner.

SUMMARY OF THE INVENTION

The present invention relates generally to an apparatus for thermal coagulation and more particularly to a system for applying heat to the endometrium of a human uterus of the type comprising a heated balloon catheter having a reciprocating piston for improved circulation of fluid within a distensible bladder. The present invention includes a heated balloon catheter having a fluid delivery tube connected to a distensible bladder. The catheter further includes a reciprocating piston which moves along a linear path within the distensible bladder to cause vigorous fluid agitation therein. The agitation caused by the piston efficiently mixes the fluid within the balloon without requiring hot fluid to circulate through the fluid delivery tube.

One embodiment of the present invention includes a perforated tubular housing secured to the distal end of a catheter. The housing slidably contains a ferromagnetic piston. The piston may be up to one half of the length of the housing. The piston is slideably mounted into the housing between two stoppers. One half of the outside of the piston housing is wrapped with an electric heating coil, creating a coiled region. When an electric is current passed through the heating coil, a magnetic field is generated. The magnetic field moves the magnetic piston into and out of the coiled region, depending upon the direction of the current. The current is reversed periodically to cause the magnetic piston to move back and forth along the piston housing. As the piston moves, fluid is moved into and out of the perforated housing and the balloon, thereby creating a circulation path for the heating fluid. Such circulation causes the fluid in the balloon to mix, minimizing the temperature differential over the surface of the balloon.

Another embodiment of the present invention also includes a perforated housing that contains a ferromagnetic piston. The piston reciprocates between two electromagnets mounted at opposite ends of the housing. Each magnet is connected in a series circuit. Each coil is wound in opposite directions so that a current causes the polarity of the magnets to be opposite at all times. An electric current is applied to the circuit which causes the piston to move toward one or the other magnets, depending upon the direction of the current. The direction of the current is continually alternated, which causes the piston to move back and forth along a reciprocating path within the perforated housing. As the piston travels along the reciprocating path, fluid is force out of the housing into the balloon and into the housing from the balloon. This causes the fluid in the balloon to mix and minimizes the temperature differential over the surface of the balloon.

In another embodiment of the present invention, the circulation assembly includes a perforated tubular housing having two stoppers mounted within opposite ends of the housing to define a piston chamber. The piston chamber contains a piston attached at a first end to an adjacent stopper by a heat memory coil formed in the shape of a spring. A steel spring connects the other end of the piston to the other stopper. The piston moves along a reciprocating path caused by periodic surges of electric current through the heat memory coil. The electricity heats the coil above a threshold temperature, which causes the causes the heat memory alloy spring to expand, allowing the steel spring coil to contract. When electric current is terminated to the heat memory coil, the heat memory coil cools below the threshold temperature, causing it to contract and causes the spring coil to expand. The expansion and contraction of the coils cause the piston to reciprocate within the housing. This in turn circulates the fluid in the balloon, thereby reducing temperature fluctuations over the surface of the balloon.

Yet another embodiment of the present invention includes balloon catheter having a piston attached to the distal end of a reciprocating rod. The rod extends from a tubular housing disposed within a balloon, through and into a handle of the balloon catheter. The proximal end of the reciprocating rod is placed within the housing and is slidably attached to a rotating mechanism disposed in the handle. The rotating mechanism may comprise a fly wheel turned by a motor mounted in the handle. As the fly wheel turns, a connecting rod converts the rotary motion of the wheel into longitudinal motion of the reciprocating rod, which causes the piston to move back and forth within the tubular housing. The reciprocating piston circulates the fluid in the balloon, thereby reducing fluctuations over the surface of the balloon.

These and other features and advantages of the present invention will become apparent from the following more detailed description, when taken in conjunction with the accompanying drawings which illustrate, by way of example, the principles of the invention.

DETAILED DESCRIPTION OF THE INVENTION

As shown in the drawings for purposes of illustration, the present invention is embodied in a heated balloon catheter apparatus having a reciprocating piston disposed within a tubular housing for circulating inflation and heating fluid within a distensible bladder. The inventive apparatus and method utilize a heated distensible bladder to treat menorrhagia in women by inserting a balloon catheter into the patient's uterus and inflating the balloon with the fluid, such as saline or aqueous sugar solution. After balloon inflation, the fluid is heated to a temperature for a period of time that coagulates, ablates, necroses, or destroys the endometrium and perhaps damages the myometrium. Such treatment of menorrhagia is desirable, because the procedure effectively curtails the excessive uterine bleeding associated with menorrhagia without requiring surgical removal of the uterus.

A successful endometrial ablation procedure requires controlling the temperature of the surface of the balloon and the fluid within. Temperature fluctuations and gradients along the surface of the balloon adversely affects physician control over endometrial necrosis. Temperature fluctuations and gradients are, in part, caused by convection currents of the fluid within the balloon and formation of a static, insulating boundary layer of fluid along the inner surface of the balloon. Vigorous mechanical circulation or agitation of fluid within the balloon improves the temperature consistency along the surface of the balloon.

Figure 1:
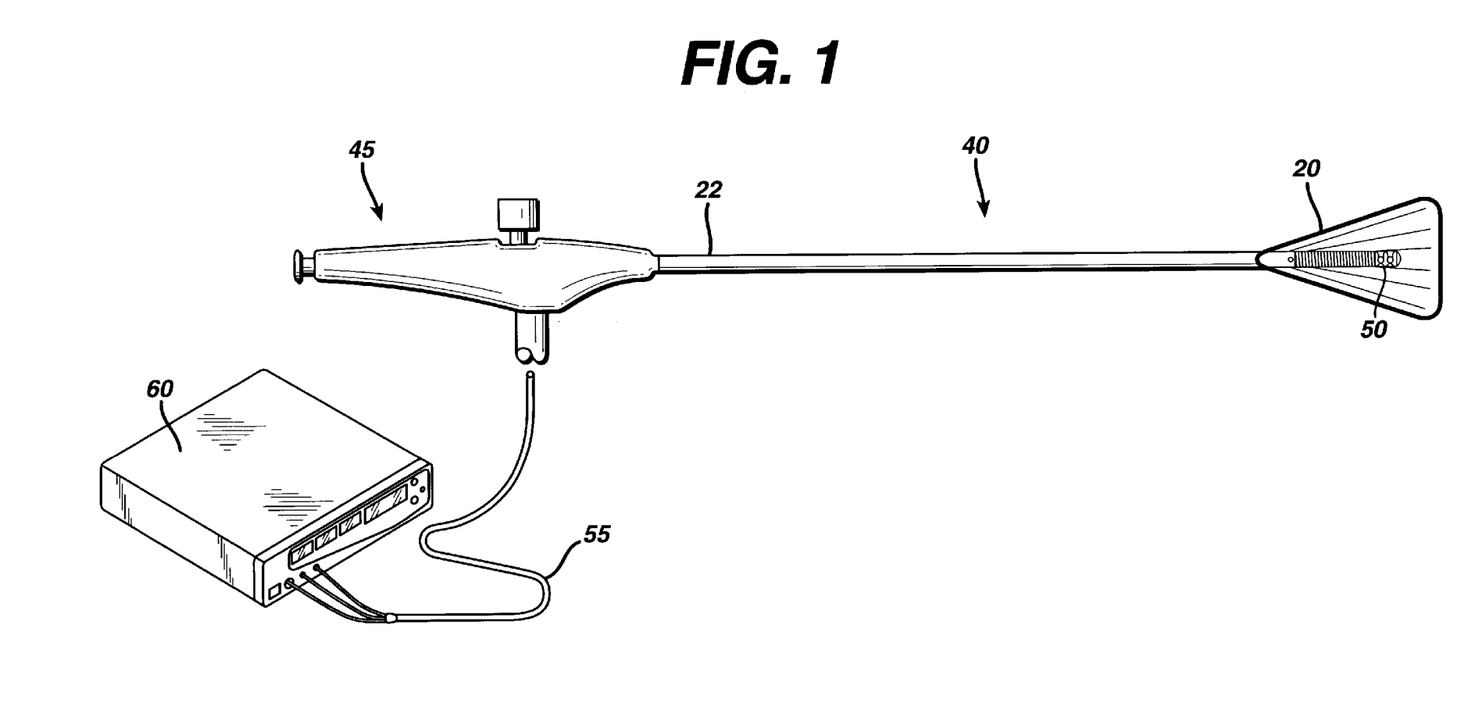
FIG. 1 is perspective view of the balloon catheter apparatus, controller and circulation assembly of the present invention.

In accordance with the present invention, and as shown in FIG. 1, a heated balloon catheter apparatus 40 having a circulation assembly 50. The balloon catheter includes a catheter or tubular member 22 for fluid delivery having a distal end disposed within a distensible bladder or balloon 20. A handle assembly 45 is secured to the proximal end of the catheter tubular member and is configured for manipulation by the physician or other user. A system controller 60 may be connected to the handle by an umbilical cable 55. Alternatively, the balloon catheter may be connected to a simple power source for heating fluid within the distensible bladder.

Figure 2:
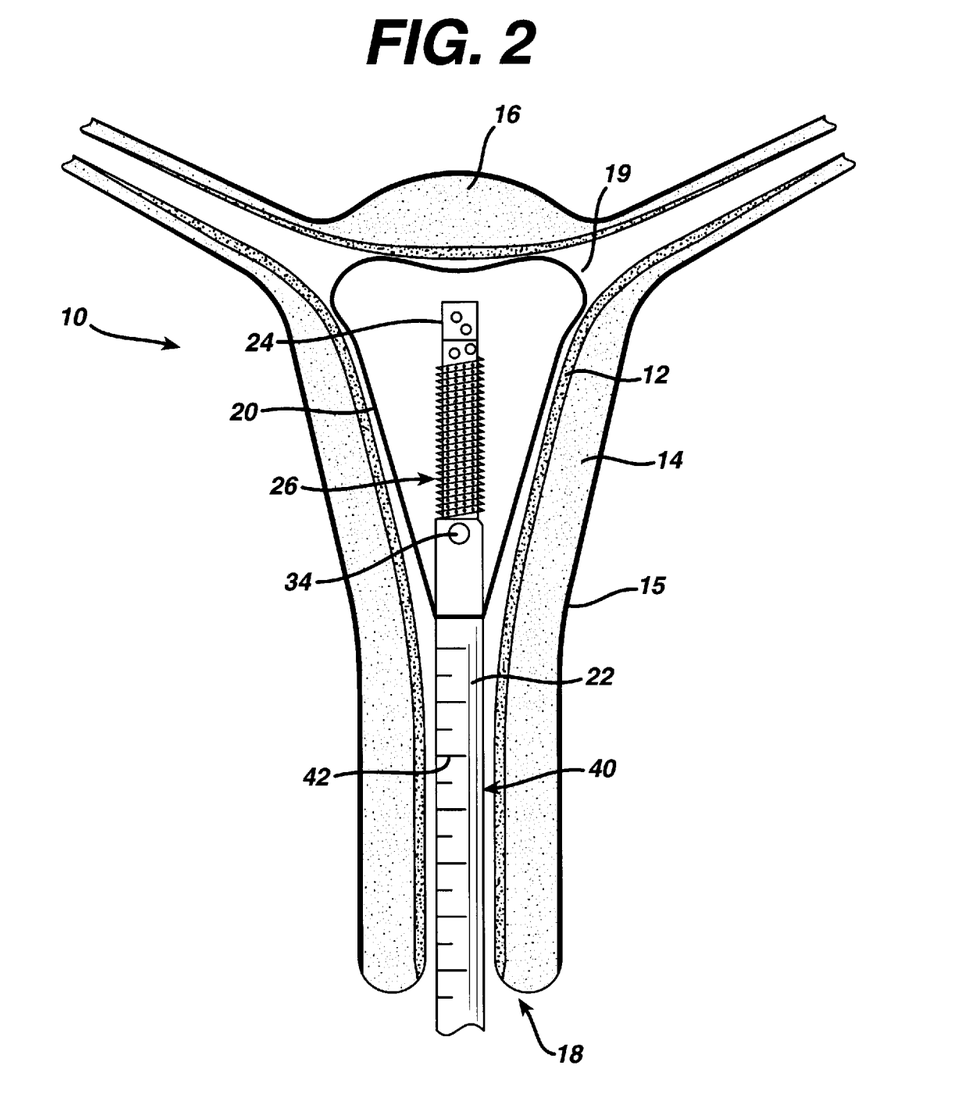
FIG. 2 is a partial cross-sectional of a heated balloon catheter apparatus of the present invention disposed within a human uterus.

With reference to FIG. 2, the distal end of the balloon catheter tubular member 22 is configured to be inserted within the uterus 10 of a human patient without traumatizing or damaging patient tissue. The uterus is comprised of three basic layers, i.e., the endometrium 12, the myometrium 14 and the outer layer or serosa 15. The balloon catheter is inserted into the uterus through the cervix 18 and proximate the fundus 16. A heating assembly 26 is disposed within the balloon 20 and is secured to the distal end of the catheter tubular member. The balloon is configured to conform to the shape of the uterus so as to provide heat transfer from the heating assembly to the endometrium. The distal portions of the balloon substantially extend into each cornu 19 of the uterus.

Also enclosed with the balloon 20 is a tubular housing 24 within which is disposed a reciprocating piston proximate a heating element 26. The piston causes the fluid to move in a circulation path around the housing and within the balloon. The circulation caused by the reciprocating piston eliminates temperature differentials along the surface of the balloon, including the portions of the balloon proximate the cornua 19.

Referring to FIG. 2, the balloon catheter shaft or tubular member 22 is formed from an elongated tubing made of semi-rigid material, for example, acrylonitrile-butadiene-styrene (ABS), polyvinyl-chloride (PVC) or polyurethane to permit easier insertion into the uterus. Such material provide the support needed to manipulate the balloon 20. The tubular member has sufficient length from the balloon to the catheter handle 45 to extend through a patient's vagina, through the cervix 18 and into the uterus 10. Placement of the apparatus may be aided by virtue of scale gradations 42 configured directly on the tubular member to indicate the depth of insertion of the balloon.

Figure 3:
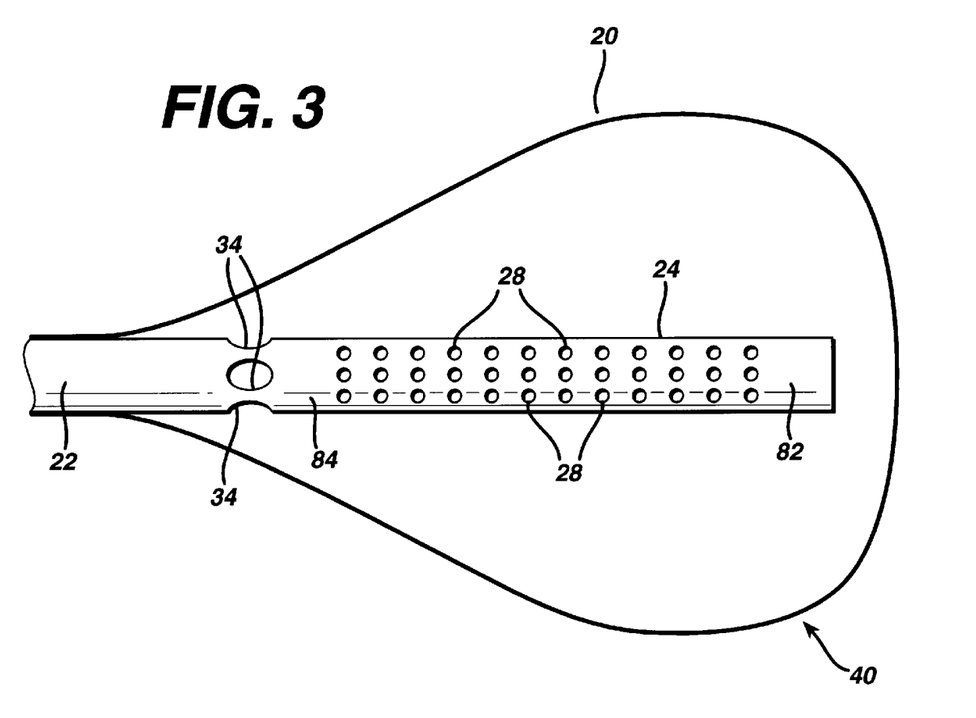
FIG. 3 is an enlarged side-sectional view of the balloon, fluid delivery tube and tubular housing of the present invention.

As shown in more detail in FIG. 3, the balloon 20 is attached to a fluid delivery tube 22 that has at least one fluid delivery port 34 that provides fluid communication between an external fill port (not shown) and the balloon. Contained within the balloon is a tubular housing 24 secured to the distal end of the catheter delivery tube. The housing has perforations or holes 38 over its surface to facilitate fluid flow in and out of a lumen or chamber within the tubular housing. A reciprocating piston is disposed within the lumen of the housing to move fluid through the perforations which extend into the lumen.

The distensible bladder or balloon 20 preferably is made of latex, silicone or other elastomeric material and has a general pear shape. It is approximately three to five centimeters long and when inflated is capable to fill the uterine cavity 17 and exert a pressure against the endometrium 12. The shape of the uterine cavity is not round, but is flattened proximate the fundus 16. Since the balloon in its inflated state conforms to the shape of the uterus, the inflated balloon will be flattened at its distal portion.

The balloon 20 must be capable of withstanding high temperatures without rupturing, and preferably have as good a heat transfer characteristic as is obtainable in such materials to provide efficient heat transfer to tissue. A distensible bladder of a sturdy, heat resistant material, such as latex rubber or silicone, has been found satisfactory. The inflation medium or heating fluid preferably should be a sterile non-toxic fluid. A five percent dextrose in water solution has been found satisfactory.

The general procedure for treating the patient according to the present invention involves inserting the uninflated balloon 20 into the vagina past the cervix 18 into the uterine cavity 17. The balloon then is filled with fluid such as saline or water 32. Fluid passes down the fluid delivery tube 22 through fluid ports 34. The fluid expands the balloon to fill the uterine cavity and exert a gentle pressure against the walls of the uterus 10. Current passes through the heating element to heat the fluid in the balloons to a desired temperature. While the fluid in the balloon is heated, a piston 30 reciprocates back and forth within the housing to cause mixing of the fluid within the balloon. The temperature is maintained for a period of time sufficient to cause thermal coagulation of the endometrium 12. Thereafter, fluid is allowed to cool to a temperature which will not burn or cause damage to patient tissue as the fluid is withdrawn from the balloon through the fluid port 34 and delivery tube 22. The balloon catheter is then removed from the body of the patient.

Figure 4:
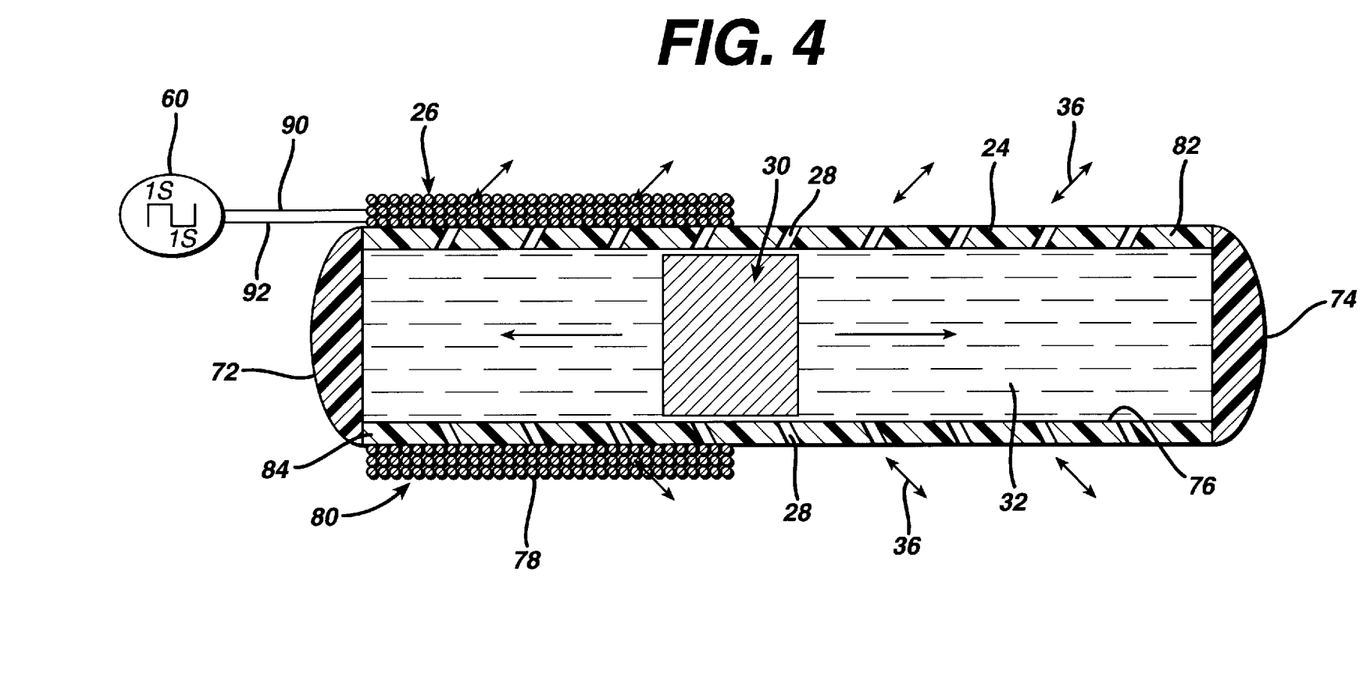
FIG. 4 is an enlarged side sectional view of the tubular housing, magnetic coil and piston of the first embodiment of the present invention.

As shown in FIG. 4, the circulation assembly of one embodiment of the present invention includes a reciprocating piston 30 disposed within a centrally located lumen or chamber 76 of the tubular housing 24 secured to the end of the fluid delivery tube 22. A heating element 26 formed of a resistive wire is wound around a portion of the outside of the housing. The heating element forms a coil which generates a magnetic field to cause movement of the piston within the lumen of the tubular housing. A plurality of perforations or holes 28 is configured along the surface of the piston housing. Movement of the piston within the lumen causes fluid to flow back and forth through the holes in the piston housing. The flow causes agitation and mixing of the fluid as it is heated. The mixing of the fluid reduces the temperature fluctuations within the balloon.

The piston housing 24 is configured from a tubular member approximately four centimeters long having a central lumen. A plurality of perforations 28 are formed within the wall of the tubular housing and extend from the outside surface of the wall to the lumen. The perforations are formed at an angle to the surface of the tubular housing. Angling the perforations causes fluid flow radially outward from the housing, as shown by the direction arrows 36.

The tubular housing 24 is preferably formed with a round cross-sectional area. Alternatively, the housing may be formed with a generally square cross-sectional area. The housing is attached to the balloon proximate the tubular housing's distal end, such that the heating element 26 is centered within the balloon 20. The housing may further be an integral part of the fluid delivery tube 22, as shown in FIG. 3, or may be affixed over or within the distal end of the fluid delivery tube.

Referring again to FIG. 4., the piston mechanism of the first embodiment of the present invention is contained within the housing 24. A pair of stoppers 72, 74 are mounted at the proximal and distal end of the housing respectively. The space within the housing defines a piston chamber 76 along which a magnetic piston 30 reciprocates. The magnetic piston is placed within the housing 24 prior to fitting the distal stopper 74 onto the distal end of the housing. The magnetic piston is made of a ferromagnetic material such as an iron-nickel alloy. It may be coated with a plastic or other material, such as polytetrafluroethylene, to eliminate corrosion and to provide a hydrophobic surface which reduces the friction of the moving piston. The piston's length should be less than half of the length of the piston chamber 76. The diameter of the piston should be selected so that the piston slides freely within the piston chamber. The piston should be sufficiently large that it is capable of pushing the fluid in and out of the chamber.

Half of the piston housing 24 extending from the proximal stopper 72 at the housing proximal end 84 is covered with a resistive wire coil 78, which may be made of copper. The coil has two functions. First, the wire serves as an electrical heater. Second, the wire coil creates a magnetic field which causes the piston to move along a reciprocating path. The reciprocation is caused by alternating the direction of the current through the coil periodically.

The polarity of the magnetic field is repeatedly alternated by the system controller 60 to move the piston 30 within the lumen 76 of the tubular housing 24. Wire leads 90, 92 from the system controller extend along the outside of the tubular housing and are electrically connected to the coil 78. The direction of the current through the coil determines whether the magnetic field 80 through and around the lumen of the tubular housing creates a positive pole at the tubular housing's distal end 82 and a negative pole at the housing proximal end 84, or whether the poles are reversed. The magnetic piston will be attracted or repelled from the portion of the tubular housing lumen within the coil, depending upon the orientation of the poles of the coil and the poles of the piston.

The coil 78 also functions as a heating element. Thus, the coil serves a dual purpose of heating the fluid and causing the piston to reciprocate. Regardless of the direction of the current, the magnetic coil becomes hot as current passes through the resistive wire of the coil. Combining the heating element with the circulation assembly 50 simplifies the structure of the balloon catheter. The simplification also contributes to creating a more narrow profile of the balloon catheter. The motion of the piston, however, is dependant upon continuous heat through the heating coils. To provide control the reciprocation of the piston independent of the fluid heating, a separate circuit may be configured in the system controller to separately provide electric current to the heating element and to the magnetic coil.

The direction of the current is periodically changed by a timed relay switch within the system controller 60, or similar mechanism as known in the art. Efficiency is maximized if the relay switch changes the circuit according to cyclical periods that are coordinated with the time it takes the piston to travel from one end of the piston chamber to the other under normal conditions. The time it takes a piston to travel from one end to another is dependant upon the physical characteristics and dimensions of the piston and the piston housing, the size of the holes, the viscosity of the fluid etc. It may be desirable to have a relay switch that has an adjustable frequency.

Figure 5:
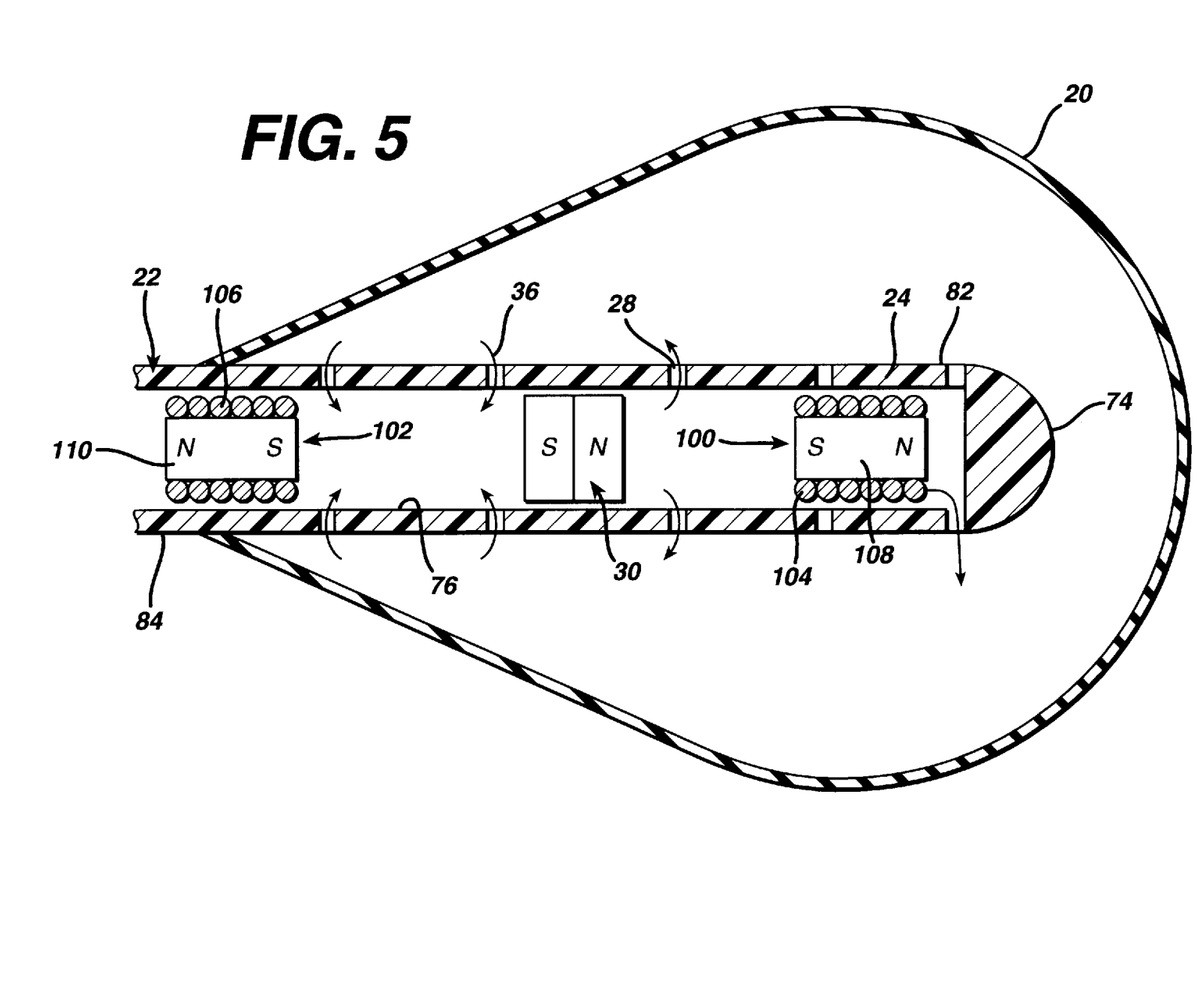
FIG. 5 is an enlarged side sectional view of the fluid delivery tube, balloon, tubular housing, magnetic coils and piston of the second embodiment of the present invention.

As shown in FIG. 5, the second alternative embodiment of the present invention includes a ferromagnetic piston 30 slidably disposed between a pair of electromagnets 100, 102 within the lumen 76 of the tubular housing 24. A distal magnet 100 and a proximal magnet 102 are contained within the distal end 82 and the proximal end 84 of the tubular housing 24, respectively. The electromagnets and piston are aligned so that the electromagnets attract and repel the piston as the polarity of the electromagnets is reversed by the system controller 60. The piston should have a diameter that will allow the magnet to slide freely through the housing.

The distal electromagnet 100 includes a resistive wire coil 104 and a ferric core 108. Similarly, the proximal electromagnet 102 includes resistive wire coil 106 wound around a ferric core 110. To ensure that each electromagnet exerts the same force, the two electromagnets should be wound with an equal number of windings in the coils, since the number of windings in the coils increases the magnetic field strength of the coils. The electromagnets are placed within the lumen of the tubular housing, which forms a piston chamber or lumen 76. If the coils are contained within the housing rather than outside the housing, the balloon catheter 40 is provided with a more narrow profile. The tubular housing is configured with perforations 28 along its surface and through to the piston chamber to facilitate fluid flow into and out of the piston chamber.

As the system controller 60 provides current to each electromagnet, a positive magnetic field (e.g., a north pole) is generated at the first end of each stationary magnet and a negative magnetic field (e.g., a south pole) is generated at the second end of each stationary magnet. The electromagnets are configured such that the positive magnetic fields will be on the inside or outside of the piston chamber for both electromagnets at the same time. For example, the resistive wire of the distal coil is wound in an opposite direction to the resistive wire of the proximal coil. The magnetic piston oriented between the two electromagnets and having a positive pole at its proximal end and a negative pole at its distal end will be attracted to the distal magnet and repelled by the proximal magnet when the positive poles are on the outside of the piston chamber. When the circuit is reversed, the magnetic piston is repelled by the proximal magnet and attracted by the distal magnet (positive poles on inside of piston chamber).

The system controller 60 is configured with a relay switch electrically connected to the electromagnet which periodically changes the polarity of the distal and proximal electromagnet. The periodic reversal of the electromagnet polarity causes the piston to reciprocate within the piston housing. The movement of the piston back and forth causes fluid to be drawn into and expelled from the piston chamber.

Figure 6:
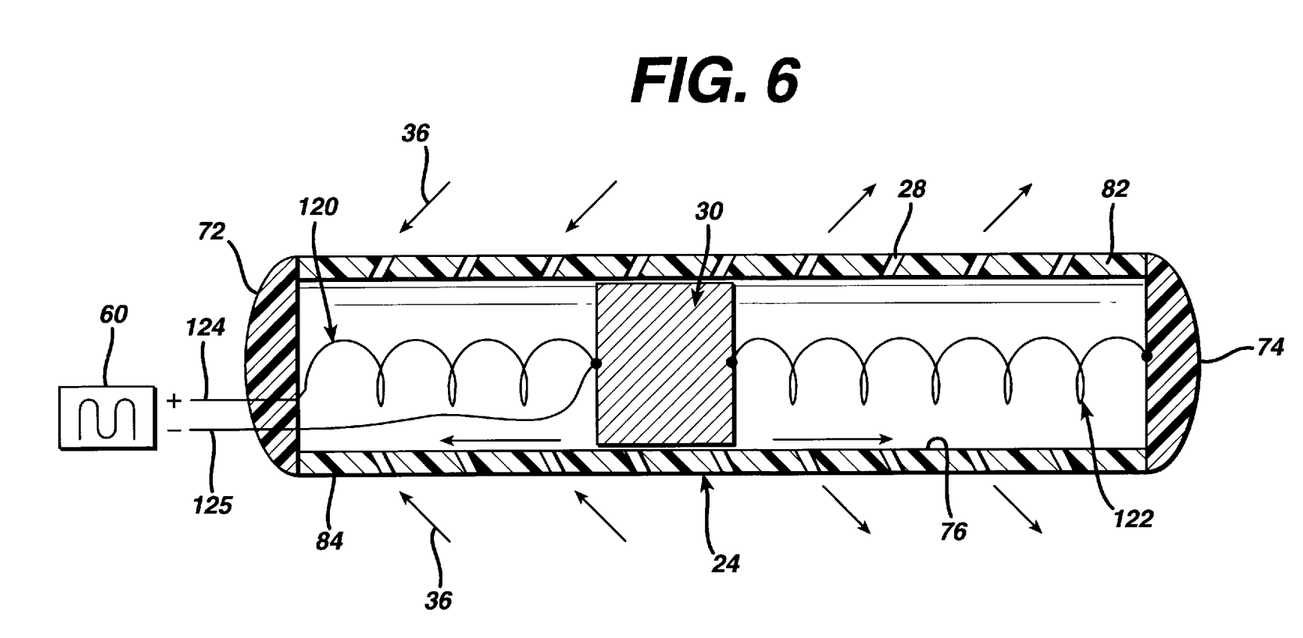
FIG. 6 is an enlarged side sectional view of the tubular housing, activation coil, spring coil and piston of the third embodiment of the present invention.

As illustrated in FIG. 6, a third embodiment of the present invention comprises a circulation assembly 50 having a heat memory alloy formed into an activation spring 120 and secured to a piston 30 which is secured to a fixed spring 122. Activation and deactivation of the heat memory alloy spring creates counter-forces to the fixed spring, causing reciprocation of the piston. Thus, in addition to electromagnetic forces, other forces can be used to move the piston within the tubular housing 24 of the balloon catheter 40.

The circulation assembly 50 of the present invention having a heat memory alloy spring 120 includes a balloon 20 in fluid communication with fluid delivery tube 22, which has at least one fluid delivery port 34. A housing 24 is formed with a plurality of perforations or holes 28 covering its surface. A proximal stopper 72 and a distal stopper 74 are mounted at the proximal end 84 and distal end 82 of the housing, respectively. A piston 30 is slideably mounted within a lumen or piston chamber 76 formed by the tubular housing.

The piston 30 is slidably mounted within the lumen of the tubular housing 24 by the activation spring 120, formed of a heat memory alloy, and by a fixed spring 122, preferably formed of a metal, such as stainless steel. For example, the piston is secured to the distal stopper 74 by the heat memory alloy spring and to the proximal stopper 72 by a steel spring. Alternatively, the activation spring may be secured to the distal stopper and the fixed spring secured to the proximal stopper. The stretched length of each spring is roughly equal to the length of the piston chamber minus the length of the piston. Each end of the heat memory alloy spring is secured to an electrical lead 124, 125 connected to the system controller 60, which cycles current to the activation spring.

One family of suitable heat memory alloys is the nickel-titanium alloys commonly known as nitinol. The properties of such alloys are well known to those skilled in the art of heat memory alloys. Suitable heat memory alloys will forcefully return to a spring form (or similar preformed shape) when the alloy is cooled below a threshold temperature. The heat memory alloy spring 120 is heated by passing a current through the leads 124, 125 connected to the heat memory alloy spring 240. The current heats the coil above a threshold temperature, which causes the heat memory alloy spring to change shape, for example, straighten from a coiled configuration. The biasing force of the contracting activating spring is configured to exceed the bias force of the fixed spring 122, causing the piston 30 to move toward the end of the tubular housing lumen 76 to which the activation spring is secured.

For example, when current is terminated to the heat memory alloy spring 120, the resulting biasing force exceeds that of the steel spring 122 and the piston 30 is pulled toward the proximal stopper 72. This movement of the piston expels fluid through the perforations 28 in the tubular housing 24 which are proximal to the piston, and draws fluid into the lumen 76 through the perforations which are distal to the piston. When the system controller initiates current flow to the activation spring, the biasing force in the fixed spring exceeds the activation spring force, and the piston is moved toward the end of the tubular housing to which the fixed spring is secured. Again, the piston moves fluid into and out of the perforations in the tubular housing wall, thereby circulating fluid through the tubular housing lumen 76 and the cavity formed by the inflated balloon 20. The alloy is configured such that the operating temperatures of the fluid in the balloon cools the alloy, assisting its transition to a state of contraction. A timed relay switch within the system controller 60, as well understood by one skilled in the art, may be electrically connected to the activation spring leads 124, 125 to reciprocate the piston.

Alternatively, the fixed spring 122 may be replaced by a second heat memory alloy spring 120 affixed to the piston 30. Both heat memory springs should be made of the same grade of wire, have similar length, equal number of radial coils, and have the same threshold temperature for changing the state of the alloy. Electrical leads from both springs are connected to the system controller 60 to provide periodic compressions of both the first spring and the second spring to cause reciprocation of the piston. Such reciprocation of the piston is accomplished by alternating electric current between the first spring and the second spring. Thus, when current is initiated to the first spring it relaxes, and the second spring pulls the piston. Then, current is terminated to the first spring and is initiated to the second spring, causing the first spring to contract. As the second spring relaxes, the piston moves in the opposite direction within the tubular housing. Thus, fluid is circulated through the tubular housing lumen 76 and the chamber formed by the balloon.

Figures 7, 7A:
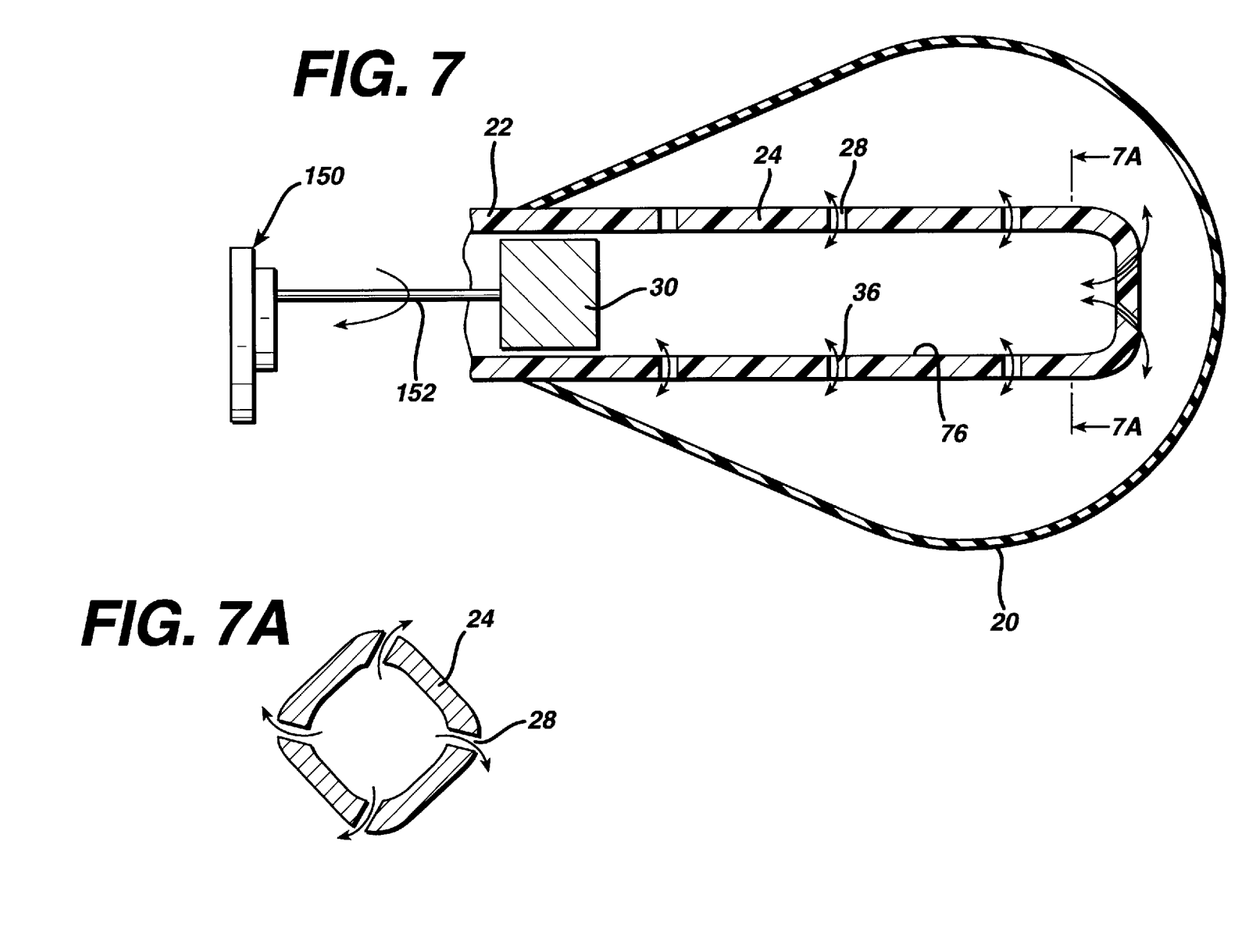
FIG. 7 is an enlarged side sectional view of the fluid delivery tube, balloon, tubular housing, cam, drive shaft and piston of the fourth embodiment of the present invention.
FIG. 7A is an enlarged cross-sectional view of the housing of FIG. 7 taken along the lines 7A—7A.

With reference to FIG. 7, the circulation assembly 50 of the balloon catheter 40 includes a reciprocating piston 30 mechanically moved by an external cam 150 and drive shaft 152. The proximal end of the piston is connected to the distal end of the drive shaft. The distal end of the drive shaft is rotatably secured to the cam. The cam preferably resides in the handle 45 of the balloon catheter, and is rotated by hand, motor or similar device. The piston and distal portion of the drive shaft reside within a piston chamber of lumen of a tubular housing 24 having a plurality of perforations 28, as shown in FIG. 7A. The balloon catheter further comprises a fluid delivery tube 22 having a proximal end secured to the handle and a distal end secured to the tubular housing. The tubular housing is disposed within a balloon secured to the distal end of the fluid delivery tube.

It will be apparent from the foregoing that, while particular forms of the invention have been illustrated and described, various modifications can be made without departing from the spirit and scope of the invention. Accordingly, it is not intended that the invention be limited, except as by the appended claims.

I claim:

1. An assembly for heating of tissue, the assembly comprising:

an elongate tubular member having a distal end and a fluid passage, said tubular member having a tubular housing formed proximate the distal end of said tubular member;

an inflatable member sealably affixed proximate the distal end of said tubular member, the tubular housing of said tubular member being disposed within said inflatable member, the tubular housing having a lumen in fluid communication with said inflatable member;

a piston slideably disposed within the lumen of the tubular housing of said tubular member; and a reciprocating assembly configured to impart periodic longitudinal motion to said piston to cause fluid movement within said inflatable member.

2. An assembly for treatment of the endometrium of a patient, the assembly comprising:

an elongate tubular member having a distal end and a fluid passage;

an inflatable member sealably affixed proximate the distal end of said tubular member; a housing secured to the distal end of said tubular member and disposed within said inflatable member, said housing having a lumen in fluid communication with said inflatable member;

a piston slideably disposed within the lumen of said housing; and a reciprocating assembly configured to cause periodic longitudinal motion of said piston to provide movement of a fluid within said inflatable member.

3. The heated balloon catheter of claim 2, wherein said reciprocating assembly is further configured to cause fluid movement within the lumen of said housing.

4. The heated balloon catheter of claim 2, wherein said housing is further configured with a plurality of perforations formed at an angle to a surface of said housing.

5. The heated balloon catheter of claim 2, wherein said piston is configured with a coating to reduce friction with said housing.

6. A heated balloon catheter for treatment of the endometrium of a patient, the heated balloon catheter comprising:

a catheter having a distal end and a fluid passage;

a balloon sealably affixed proximate the distal end of said catheter;

a housing mounted within said balloon and to the distal end of said catheter, said housing having a lumen in fluid communication with said balloon;

a magnetic piston slideably disposed within the lumen of said housing; and a coil positioned proximate the distal end of said catheter, said coil configured to impart periodic longitudinal motion to said piston to cause fluid movement within said balloon.

7. The heated balloon catheter of claim 6, wherein said coil is further configured to heat fluid within said balloon.

8. The heated balloon catheter of claim 7, wherein said housing is further configured with a plurality of perforations formed at an angle to the surface of said housing.

9. The heated balloon catheter of claim 8, wherein said magnetic piston is configured with a coating to reduce friction with said housing.

10. A heated balloon catheter for treatment of the endometrium of a patient, the heated balloon catheter comprising:

- a fluid delivery tube having a distal end and a fluid passage;
- a balloon sealably affixed proximate the distal end of said fluid delivery tube;
- a tubular housing located at the distal end of said fluid delivery tube, said housing being disposed within said balloon and having a lumen in fluid communication with said balloon;
- a piston slideably disposed within the lumen of said housing, said piston being formed from permanent magnetic material;
- a first electromagnet positioned proximate a first end of said tubular housing; and
- a second electromagnet positioned proximate a second end of said tubular housing,
- wherein said first electromagnet and said second electromagnet are configured to cause periodic longitudinal motion of said piston to provide fluid movement within said balloon.

11. The heated balloon catheter of claim 10, wherein said first electromagnet is further configured to heat fluid within said balloon.

12. The heated balloon catheter of claim 11, wherein said second electromagnet is further configured to heat fluid within said balloon.

13. The heated balloon catheter of claim 12, wherein said piston is configured with a coating to reduce friction with said housing.

14. A heated balloon catheter for treatment of the endometrium of a patient, the heated balloon catheter comprising:

- an elongate tubular member having a distal end and a fluid passage;
- a balloon sealably affixed proximate the distal end of the tubular member;
- a housing mounted within said balloon and to the distal end of said tubular member and having a lumen in fluid communication with said balloon;
- a piston slideably disposed within the lumen of said housing;
- a first spring secured to a first end of said housing and secured to a first end of said piston, wherein said first spring is formed from a heat memory alloy; and
- a second spring secured to a second end of said housing and secured to a second end of said piston, wherein said first spring and said second spring are configured to cause periodic longitudinal motion of said piston to provide circulation of a fluid within said balloon.

15. The heated balloon catheter of claim 14, wherein said second spring is formed from stainless steel.

16. The heated balloon catheter of claim 14, wherein said second spring is formed from a heat memory alloy.

17. The heated balloon catheter of claim 16, wherein said tubular housing is further configured with a plurality of perforations formed at an angle to a surface of said housing.

18. The heated balloon catheter of claim 17, wherein said piston is configured with a coating to reduce friction with said housing.

19. A heated balloon catheter for treatment of the endometrium of a patient, the heated balloon catheter comprising:

- a fluid delivery tube having a distal end and a fluid passage;
- a balloon sealably affixed proximate the distal end of said fluid delivery tube;
- a tubular housing located at the distal end of said fluid delivery tube, said housing being disposed within said balloon and having a lumen in fluid communication with said balloon;
- a piston slideably disposed within the lumen of said housing;
- a drive shaft having a first end secured to said piston and partially disposed within said tubular housing and said fluid delivery tube; and
- means for causing longitudinal motion to said drive shaft so as to cause periodic longitudinal motion of said piston to provide movement of a fluid within said balloon.

20. The heated balloon catheter of claim 19, wherein said means for causing longitudinal motion to said drive shaft includes a cam external to said fluid delivery tube, wherein the cam is secured to a second end of said drive shaft.

21. The heated balloon catheter of claim 20, wherein said tubular housing is further configured with a plurality of perforations formed at an angle to the surface of said housing.

22. The heated balloon catheter of claim 21, wherein said piston is configured with a coating to reduce friction with said housing.

* * * * *